United States Patent [19]

Giaever

[11] 4,172,827

[45] Oct. 30, 1979

[54] METHOD FOR CONCENTRATION AND PURIFICATION OF ANTIGENS AND ANTIBODIES

[75] Inventor: Ivar Giaever, Schenectady, N.Y.

[73] Assignee: General Electric Company, Milwaukee, Wis.

[21] Appl. No.: 608,329

[22] Filed: Aug. 27, 1975

Related U.S. Application Data

[63] Continuation-in-part of Ser. No. 266,278, Jun. 26, 1972, abandoned.

[51] Int. Cl.$^2$ .................. C07G 7/00; G01N 21/06; G01N 33/16
[52] U.S. Cl. .................. 260/112 R; 23/230 B; 260/112 B; 260/112.7; 260/123.7; 424/12; 424/85; 424/88; 427/250; 428/336; 428/434; 428/469; 428/474; 435/7
[58] Field of Search .................. 260/112 R, 112 B; 424/85, 88, 12

[56] References Cited

U.S. PATENT DOCUMENTS

| | | | |
|---|---|---|---|
| 2,666,355 | 1/1954 | Trurnit | 23/230 R X |
| 3,171,783 | 2/1965 | Fisk | 424/12 |
| 3,236,732 | 2/1966 | Arquilla | 424/8 |
| 3,313,706 | 4/1967 | Lembke et al. | 424/9 |
| 3,492,396 | 1/1970 | Dalton et al. | 424/12 |
| 3,639,558 | 2/1972 | Csizmas | 424/12 |
| 3,639,559 | 1/1972 | Tax | 424/12 |
| 3,646,346 | 2/1972 | Catt | 424/12 X |
| 3,658,982 | 4/1972 | Reiss et al. | 424/12 |
| 3,697,645 | 10/1972 | Meier et al. | 424/85 |

OTHER PUBLICATIONS

J. Am. Chem. Soc. 59, p. 1406 (1937), Langmuir et al.
Fed. Proceedings, vol. 30, pp. 1494–1502 (1971), Vroman et al.
Helvetica Chemica Acta., 54 (Fasc. 4), pp. 1208–1217 (1971), Rothen et al.
Press release, G. E., Nov. 22, 1972.

*Primary Examiner*—Howard E. Schain
*Attorney, Agent, or Firm*—Morgan, Finnegan, Pine, Foley & Lee

[57] ABSTRACT

In carrying out a purification and/or concentration step of antigens or antibodies, a substrate is immersed in a first aqueous medium containing a specifically reacting antigen to coat said substrate with a monomolecular layer of said specifically reacting antigen. The resulting coated substrate is then immersed in a second aqueous medium containing immunologically reactive antibody specific to the antigen in the first aqueous medium to complex said immunologically reactive antibody with said specifically reacting antigen. The resulting substrate is then immersed in a reagent capable of cleaving the immunological bond between said immunologically reactive antibody and said specifically reacting antigen and forming a solution of said immunologically reactive antibody in the immunological bond-cleaving solution and leaving said specifically reacting antigen coated on said substrate. The method can be reversed for preparing a purified concentration of an immunologically reactive antigen whereby a specifically reacting antibody is substituted for the antigen and the corresponding immunologically reactive antigen is substituted for the antibody.

37 Claims, 8 Drawing Figures

METHOD FOR CONCENTRATION AND PURIFICATION OF ANTIGENS AND ANTIBODIES

CROSS-REFERENCE TO RELATED APPLICATION

This application is a continuation-in-part application of application Ser. No. 266,278 entitled "Method and Apparatus for Detection and Purification of Proteins and Antibodies" filed June 26, 1972, now abandoned.

FIELD OF THE INVENTION

This invention relates to method and apparatus for concentration and purification of antigens and antibodies. More particularly, this invention relates to concentration and purification of antigens and antibodies where the antigen-antibody reaction takes place at the surface of a substrate.

BACKGROUND OF THE INVENTION

Publications having subject matter which relates to the present invention primarily as background are "Optical Measurement of the Thickness of a Film Adsorbed from a Solution", authors Irving Langmuir et al, Journal of the American Chemical Society, Vol. 59 (July-December 1937) page 1406; and "Interactions Among Human Blood Proteins at Interfaces", Leo Vroman et al, Federation Proceedings, Vol. 30, No. 5 (Sept.-Oct. 1971) pages 1494–1502.

Immunological reactions are highly specific interactions in which an antigen combines with an antibody specific to the antigen to form an immunological complex. Immunological reactions taking place within a biological system such as an animal are vital to the animal in combating disease. In a biological system, the entry of a foreign protein, i.e., the antigen, causes the biological system to produce the specific antibody proteins to the antigen in a process not fully understood at this time. The antibody protein molecules have available chemical bonding sites which complement those on the antigen molecule and so the antigen and antibody combine to form an immunologically complexed protein.

Antibodies are produced by biological systems in response to invasion thereof by foreign proteins. Hence, the detection of antibodies present in a biological system is of medical diagnostic value in determining the antigens to which the system has been exposed. Conversely, the detection of certain antigens of a biological system also has medical diagnostic value; examples of diagnostic detection of antigens include detection of HCG protein molecules in urine as a test for pregnancy, and detection of hepatitis associated antigen molecules in blood of prospective blood donors.

In addition to the immunological reaction which occurs between specific protein antigens and specific protein antibodies resulting in the formation of a protein antigen-protein antibody complex, other immunological complexing reactions between immunologically reactive antigens and antibodies are also contemplated by this invention. In addition, specific reactions between other biological particles, such as enzymes and their substrates, are also among the methods contemplated herein and are embraced by the term "immunological reaction" as used herein. Furthermore, the terms "antigen" and "antibody" as used herein are intended to encompass such terms as enzymes, substrates of enzymes, and similar biological particles. As will also be seen, the method is versatile enough to permit substitution of a specific antibody for the corresponding antigen and the antigen for the corresponding specific antibody.

For instance, the following systems include biological particles which are capable of undergoing the immunological reactions described herein:
  Viruses
  Bacteria and Bacterial toxins
  Fungi
  Parasites
  Animal tissue
  Animal body fluids, and the like.

With respect to viruses, the antigens are viral cultures, or parts thereof, and the antibody specific thereto can be produced by administration to a living host. Illustratively, antigen-antibody complexes in the following virus systems are useful in the herein disclosed procedure:
  Rubella virus culture (antigen) - Rubella virus antibody;
  polio virus culture (antigen) - polio virus antibody;
  vesicular stomatitis virus (VSV) culture (antigen) - VSV antibody.

Regarding bacteria and bacterial toxins, the antigens are the particular bacteria or bacterial toxin, or parts thereof, and the antibody is produced by injection into a living host. The following are illustrative examples of antigen-antibody pairs which can be used in the present method:
  tetanus toxoid suspension (antigen) - tetanus antibody;
  diphtheria toxin suspension (antigen) - diphtheria antibody;
  Neisseria gonorrhoeal suspension (antigen) - gonorrhea antibody;
  Treponema pallidum suspension (antigen) - syphilis antibody.

As for fungi, the antigens are antigenic extracts of fungal suspensions and the antibody is the fungal antibody produced by injection into a living host. Antigen-antibody complexes of fungi systems are illustrated by the following:
  Aspergillus extract suspension (antigen) - aspergillus fungus antibody;
  Candida extract suspension (antigen) - candida fungus antibody.

Antigens and antibodies in parasite systems are obtained in a similar fashion to those of fungi. The system Toxoplasma gondii extract (antigen) - Toxoplasma gondii antibody is a typical example.

By the term polysaccharides is meant a system wherein the antigen is a carbohydrate antigen. An example of such an antigen-antibody containing system is pneumococcus polysaccharides (antigen) - Pneumococcus antibody.

In addition to the typical enzyme - enxyme substrate reaction which is intended to be covered herein, enzymes themselves, or parts thereof may be utilized as antigens and the antibody is the particular enzyme antibody elaborated by a living host after injection. Illustrative antigen-antibody complexes of enzyme systems are:
  Trypsin extract - trypsin antibody
  chymotrypsin extract - chymotrypsin antibody
  pepsin extract - pepsin antibody
  ribonuclease extract - ribonuclease antibody
  thrombin extract - thrombin antibody amylase extract - amylase antibody
penicillinase extract - penicillinase antibody With respect to hormones, the antigenic constituent is usually found in a hormone extract and the antibody is the particular hormone antibody elaborated by the living organism after injection. An exemplary antigen-antibody complex is:

insulin - insulin antibody

As presently practiced, both the collection and purification and the diagnostic utilization of immunologically reactive antigens and antibodies rely upon the complexing of the antigen and antibody specific to the antigen. The classic example of these diagnostic uses is the blood typing procedure in which blood samples are mixed with A and B type serum antibodies and blood type is determined by observing any agglutination occurring in the blood samples. The human chorionic gonadotrophin protein pregnancy test as currently practiced is an inhibition test. The test is performed by mixing a quantity of HCG anti-serum into a urine specimen. A plurality of polystyrene spheres which have been coated with HCG protein are then introduced into the previously prepared urine specimen. The polystyrene spheres will agglutinate if, but only if, HCG protein is absent from the urine specimen. If HCG protein is absent from a urine specimen, the HCG protein on the polystyrene spheres complexes with the HCG anti-serum previously introduced in the urine specimen and the spheres agglutinate. If, on the other hand, HCG protein is present in the urine specimen in sufficient quantity, it complexes with the previously introduced HCG anti-serum forming a complex which precipitates out of the specimen so that the previously introduced anti-serum is no longer available to complex with the HCG protein on the spheres to cause agglutination thereof. The present HCG protein pregnancy test could be simplified by adhering HCG anti-serum onto the polystyrene spheres and directly testing a urine specimen. In this case, the polystyrene spheres would agglutinate if, but only if, HCG protein is present in the specimen.

It appears that the reason this simpler procedure has not been employed is that the available HCG anti-sera are complex mixtures containing a large proportion of constituents other than HCG antibodies. The additional effort required in the prior art to extract the antibodies from the HCG anti-sera made the inhibition test, utilizing sera directly, preferable in the prior art. However, in accordance with one embodiment of this invention, a procedure is provided whereby HCG antibodies are efficiently separated from sera and, which procedure, furthermore, produces diagnostic apparatus whereby the simpler, direct test is performable.

The present procedure for obtaining purified concentrations of antibodies comprises the steps of stimulating the production of antibodies in an animal by introducing the antigen into the animal's system, obtaining blood serum from the animal which contains the antibodies in a dilute form, and mixing a quantity of the specific antigen into the serum. The mixture of antigen and antibody complexes and precipitates out of the serum solution. The remaining constituents of the serum are drawn off and the antibody-antigen precipitate is dissolved in an acid which severs the complexing bonds. At this point one has a solution of antigen and antibody molecules in acid. Since the antibody and antigen molecules have differing physical characteristics, for example, weight, they may be separated from each other by mechanical means, for example, by centrifuging.

It is known that the antibody-antigen complexing reaction will take place when an antigen is adsorbed at a surface. The complexing reaction at a surface has been observed by means of an ellipsometer.

A principal object of this invention is to provide method and apparatus for concentrating and purifying antigens and antibodies by means of controlled immunological reactions occurring at a surface.

SUMMARY OF THE INVENTION

In accordance with this invention, a wafer of substrate material is first immersed in an aqueous medium, e.g. a solution or suspension, which contains a first antigen so that a monomolecular layer of such first antigen adheres to the substrate. The substrate coated with the first antigen is then immersed in a second aqueous medium, which is known to contain the specifically reacting antibody to the first antigen. The specifically reacting antibody, and only the specifically reacting antibody, forms a second monomolecular layer overlying the monomolecular layer of the first antigen on the substrate. Then, the bi-molecular coated substrate is immersed in a reagent capable of cleaving the immunological bond between the two layers and provides for the collection of the specifically reacting antibody in purified form in the immunological bond-cleaving solution. The procedure can, of course, be reversed by starting with an aqueous medium containing the antibody and can thus be utilized to produce purified or concentrated antigen.

The features of this invention sought to be protected are set forth with particularity in the appended claims. The invention, together with further objects and advantages thereof, may be understood from a reading of the following specification and appended claims together with the accompanying drawings.

DETAILED DESCRIPTION OF THE INVENTION

Figure 1:
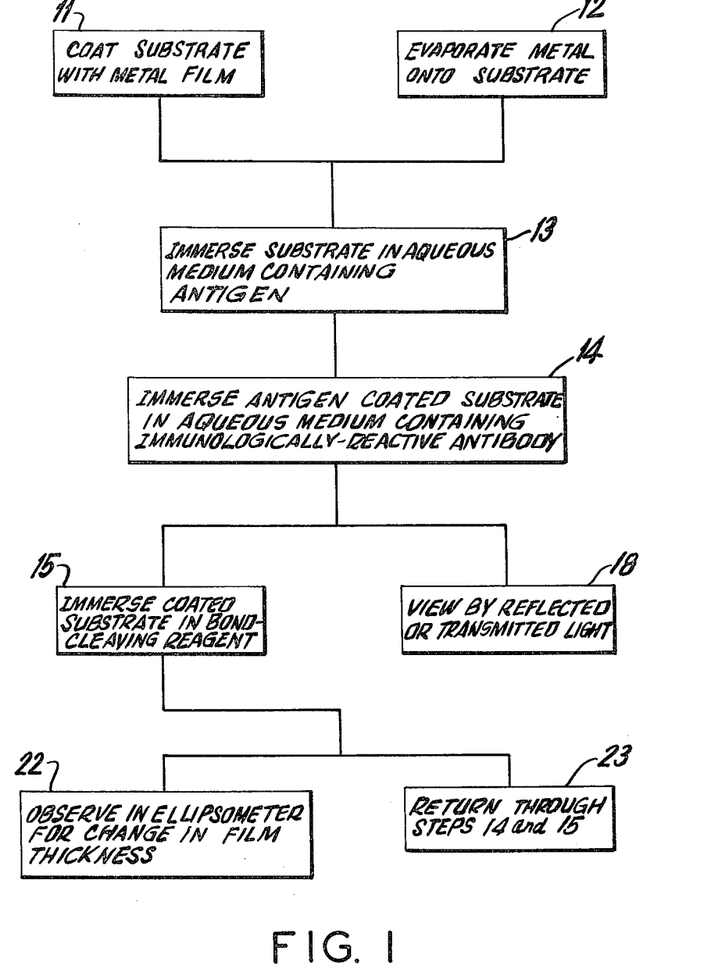
FIG. 1 is a flow chart illustrating the process steps of the various embodiments of this invention.

FIG. 1 is a flow chart illustrating the process steps involved in practicing this invention. In reading the flow chart from top to bottom, each vertical level represents one time sequential step of the process. The appearance of several steps arrayed horizontally at a given vertical level in the flow chart indicates the alternative performance of one of the indicated steps at the indicated sequential position in accordance with the various embodiments of this invention.

In accordance with the first embodiment of this invention, the process begins at block 13 of FIG. 1 in which a wafer of substrate material which may be metal, glass, mica, plastic, fused silica, quartz, or similar material, possibly in the form of a metallized glass slide, is immersed in an aqueous medium containing a first biological constituent of interest. This first biological constituent of interest may be biologically an antigen, which is to be used to purify its corresponding specifically reacting antibody. The first antigen adsorbs onto the substrate in a monomolecular layer. Any antigen or antibody will adsorb in such monomolecular layer and no further adsorption will take place. That is, the antigen or antibody will attach to the substrate, but will not attach to itself. After a monomolecular layer of antigen has formed over the surface of the substrate, the coated substrate is removed from the aqueous medium containing the first antigen. The time required to completely coat the substrate is a function of the concentration of the antigen in the aqueous medium and the degree of agitation of the aqueous medium. As an example, a 1 percent bovine serum albumin solution completely coats a slide in approximately 30 minutes with a monomolecular layer. The next step, illustrated in block 14 of FIG. 1 is to immerse the coated substrate in an aqueous medium containing the specifically reacting antibody to the first antigen. This aqueous medium may, and typically does, contain many constituents in addition to the specifically reacting antibody. However, no antigen or antibody other than the specifically reacting antibody will adhere to the first layer on the substrate. Of course, as is known, certain biological substances may adhere by a phenomenon known as non-specific sticking. Such substances are found in sera, etc. There are a number of ways to minimize non-specific sticking, the most convenient of which appears to be in diluting the media carrying such substances. In any event, if the specifically reacting antibody is not present, the substrate following immersion in the aqueous medium will still contain only a monomolecular layer thereon. If, on the other hand, the specifically reacting antibody is present in the aqueous medium, immunological complexing between the first antigen and its specifically reacting antibody will take place and the substrate will, after a time, have a bimolecular layer thereon. It is to be noted that the steps illustrated in blocks 13 and 14 of FIG. 1 are common to all of the embodiments of this invention. The time required for the adhesion of a complete second molecular layer onto the coated substrate is again a function of the concentration of specifically reacting antibody in the aqueous medium. For antibodies in blood serum, this time may be as long as one day or as short as minutes depending upon the concentration. The next step is to immerse the coated substrate in a reagent capable of cleaving immunological bonds. Such a reagent can be a weak acid solution, a base solution or a strong salt solution, and the like as illustrated in block 15 of FIG. 1. As further detailed in copending application Ser. No. 266,278, this step can be used for diagnostic purposes by simultaneously observing the coated substrate in an ellipsometer as illustrated in block 22 of FIG. 1. While the formation of the specifically reacting layer on the first antigen coated substrate may take an extended period of time, the immunological bond between the two biological constituents is severed very quickly by the immunological bond-cleaving solution. Accordingly, the observation made with the ellipsometer can be the relatively simple observation of change of film thickness rather than the more complicated measurement of absolute thickness. At the same time, observing the stripping away of the specifically reacting antibody layer by action of the immunological bond-cleaving reagent may be performed much more rapidly than the prior art method of observing the building of the specifically reacting protein layer. Accordingly, a large plurality of test slides may be prepared in accordance with block 13 and each exposed to one of a large plurality of serum samples as indicated in block 14, and then in a short time each test slide may be examined serially in accordance with blocks 15 and 22 to determine which of the serum samples contained the specifically reacting antibody to the first antigen. Since the cleaving reagent will not strip the first antigen from the substrate, those coated substrates which were immersed in aqueous media which did not contain the specifically reacting antibody will exhibit no change of film thickness when immersed in the cleaving reagent and observed in an ellipsometer. On the other hand, those which were immersed in an aqueous medium which did contain the specifically reacting antibody will exhibit approximately a factor of 2–5 change in thickness when immersed and observed in an ellipsometer. Each observation can be made in a few minutes thereby providing an efficient, and therefore diagnostically significant, test procedure.

This invention, more importantly, also provides for the concentration and purification of antigens or antibodies and comprises the steps illustrated in FIG. 1 at blocks 13, 14, 15, and 23. The substrate is first immersed in aqueous medium containing the available antigen of the antigen-antibody pair as illustrated in block 13. In the usual case, this will be the antigen, but this invention is not dependent upon the biological identity of the first biological constituent. The coated substrate produced in accordance with block 13 of FIG. 1 is then immersed in aqueous medium containing the specifically reacting antibody to the first antigen as shown in block 14. In the usual case, the specifically reacting biological constituent will be an antibody and the aqueous medium employed in block 14 will be the blood serum of an animal which has been exposed to the antigen. The substrate, now coated with a bimolecular layer, is next immersed in the cleaving reagent as shown in block 15 of FIG. 1 which strips the specifically reacting antibody layer from the first antigen layer. At this point the substrate is coated with a monomolecular layer of the first biological constituent and a purified solution of specifically reacting antibody in the cleaving reagent has been provided. The next step, as shown in block 23 of FIG. 1, is to return the substrate with its first layer adhering thereon to the aqueous medium containing the specifically reacting antibody to pick up a second layer thereof which is again stripped by the cleaving reagent thereby increasing the concentration of specifically reacting antibody. This process is continued and provides for the collection of a concentration of pure specifically reacting antibody in the cleaving reagent bath. The process can of course be reversed, i.e. started with antibody, to provide purified or concentrated antigen.

Figure 2A:
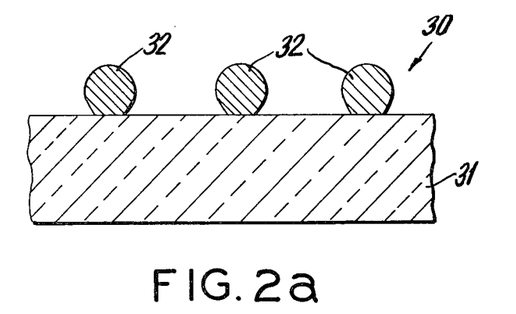
FIGS. 2a, 2b, and 2c are elevation views of an apparatus illustrating a visually observable immunological reaction.
Figure 2B:
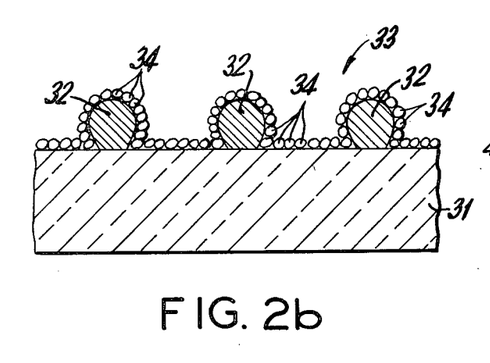
Figure 2C:
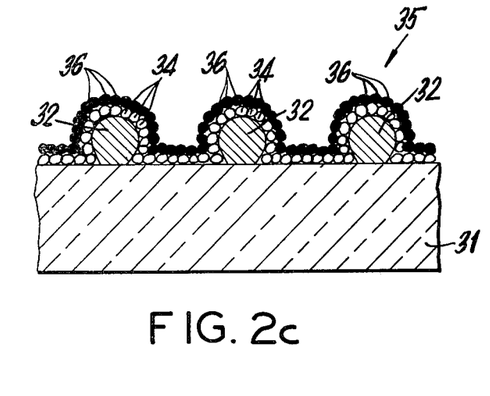

A method of visually determining the presence of antigen or antibody during the purification method is illustrated in FIG. 2. The substrate which must be a light transmissive substrate such as glass, plastic, fused silica, mica, quartz, or the like, and is preferably glass, with microscope slides being a conveniently available source, is first coated with a plurality of metal globules by evaporating a metal, for example, indium, onto the substrate as indicated in block 12 of FIG. 1. A detailed discussion of substrate metallization is found in copending patent application Ser. No. 384,113 entitled "Method and Apparatus for Detection and Purification of Proteins and Antibodies" filed July 30, 1973 having a common applicant and assignee. For example, the indium is evaporated slowly from a tantalum boat onto the glass substrate in an ordinary vacuum of about $5 \times 10^{-5}$ mm of mercury. Because the indium atoms have high mobility on the surface of the substrate and do not wet the glass substrate significantly, the indium evaporated into the substrate agglomerates into small particles. Any metal having similar characteristics so that it will form globules on the substrate when evaporated thereon may be used. In addition to indium, gold, silver, tin, bismuth, and lead have been successfully used. The evaporation of metal is continued until the substrate appears light brown in color. At this point, the metal globules have diameters on the order of 1000 Å. The precise size of the globules is not critical but they must have diameters equal to a large fraction of one of the wavelengths of visible light. The next step is to immerse the globule-covered substrate in an aqueous medium containing a first antigen as illustrated in block 13 of FIG. 1. The first antigen again adheres in a monomolecular layer over the substrate and the metal globules thereon. When a monomolecular layer has formed, the coated substrate may be used to test aqueous media for the presence of a specifically reacting antibody to the first antigen by immersing the coated substrate in the aqueous medium as indicated in block 14 of FIG. 1. If the specifically reacting antibody was present, the substrate and metal globules have a bimolecular layer adhering thereto, if the specifically reacting antibody was not present, only a monomolecular layer overlies the substrate and metal globules. The coated substrate is then viewed by either reflected or transmitted light as indicated in block 18 of FIG. 1 and a determination is made from the appearance of the coated substrate as to the thickness of the layer adhering thereto and accordingly as to the presence or absence of the specifically reacting antibody. The detection of antibody layers corresponds to variations in the shade of brown which is observed in the coated substrate. These variations are quite pronounced and the detection of layers is therefore a simple straight forward procedure. The particles alone on the substrate appear as a first shade of brown, the particles coated with a monomolecular layer appear as a darker shade of brown, and the particles covered with a bimolecular layer appear as a still darker shade of brown. This detection method is based on the fact that electromagnetic radiation is scattered to a large degree by conducting spheres having diameters equal to a large fraction of a wavelength of the incident energy and that in the case of scattering from such spheres, the scattering is strongly influenced by a thin dielectric coating applied to the spheres.

FIG. 2 is a highly magnified elevation view of a portion of apparatus in accordance with the embodiment just described. FIG. 2 shows a portion of substrate material 31 having a plurality of globules of evaporated metal 32 attached thereto. After immersion in an aqueous medium containing a first antigen, the slide segment comprising substrate 31 and metal globules 32 is coated with a monomolecular layer of molecules 34 of the first antigen as indicated in FIG. 2 generally at 33. If the apparatus indicated generally at 33 is exposed to specifically reacting antibody to the antigen of molecules 34, the apparatus will acquire the appearance indicated generally at 35 in which substrate 31 and metal globules 32 are coated with a bimolecular layer comprising the molecules 34 of the first antigen forming a first monomolecular layer overlying substrate 31 and globules 32 and a second monomolecular layer of antibody consisting of the molecules 36 of the specifically reacting antibody to the first antigen, immunologically bonded to the molecules of the first antigen or antibody and overlying the first layer, the metal globules and the substrate.

Figure 3A:
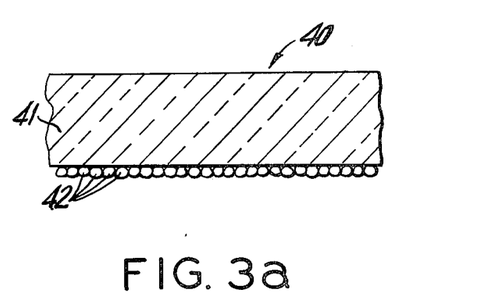
FIGS. 3a, 3b, and 3c are elevation views of apparatus useful for the purification and concentration of antigens and antibodies in accordance with one embodiment of this invention.
Figure 3B:
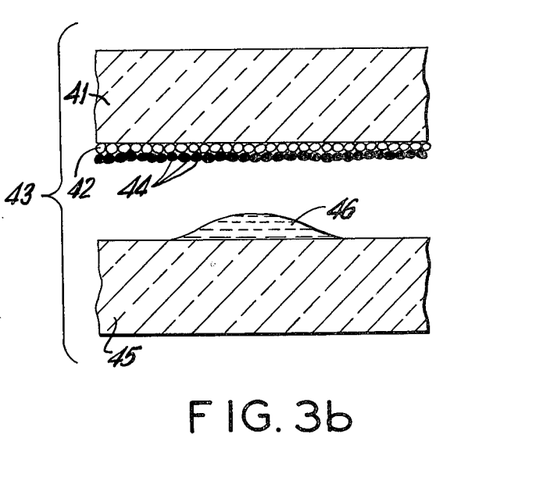
Figure 3C:
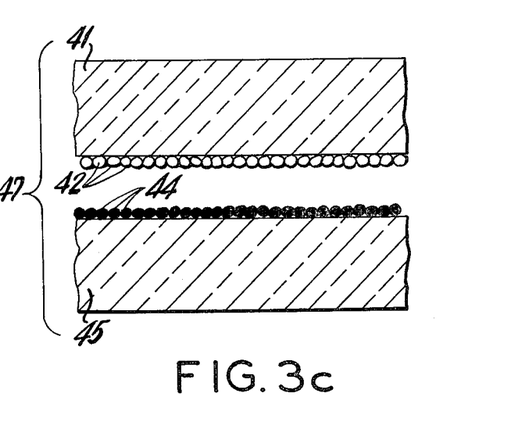

FIG. 3 is a highly magnified sectional elevation view of apparatus useful for diagnostic purposes and for the purification and concentration of antigens and antibodies in accordance with this invention. Indicated generally at 40 is a substrate 41 coated with a monomolecular layer of antigen molecules 42 which has been prepared as discussed above. Indicated generally at 43 is substrate 41 and antigen layer 42 to which has been immunologically bonded a second monomolecular layer of antibody molecules 44 of the specifically reacting antibody to molecules 42 in accordance with the procedures discussed above. A second substrate 45 has thereon a drop 46 of a cleaving reagent solution. The mutually facing surfaces of substrates 41 and 45 having thereon respectively a bimolecular layer and a drop of, for example, citric acid in a 0.1 normal solution, are then physically brought into contact with each other. In accordance with this invention, the weak acid drop 46 severs the immunological bonds between molecules 42 and molecules 44 without affecting the biochemical characteristics of either biological constituent and without severing the adhesion bond between the first antigen molecules 42 and substrate 41. When substrates 41 and 45 are again separated as indicated generally at 47, substrate 41 has adhering thereon a monomolecular layer of first antigen molecules 42 and substrate 45 has adhering thereon a monomolecular layer of specifically reacting antibody molecules 44. Substrate 41 with molecules 42 thereon may then be used to repeat the process producing another substrate coated with a monomolecular layer of specifically reacting antigen or antibody, while substance 45 with the purified antibody molecules 44 may be utilized for many purposes.

Figure 4:
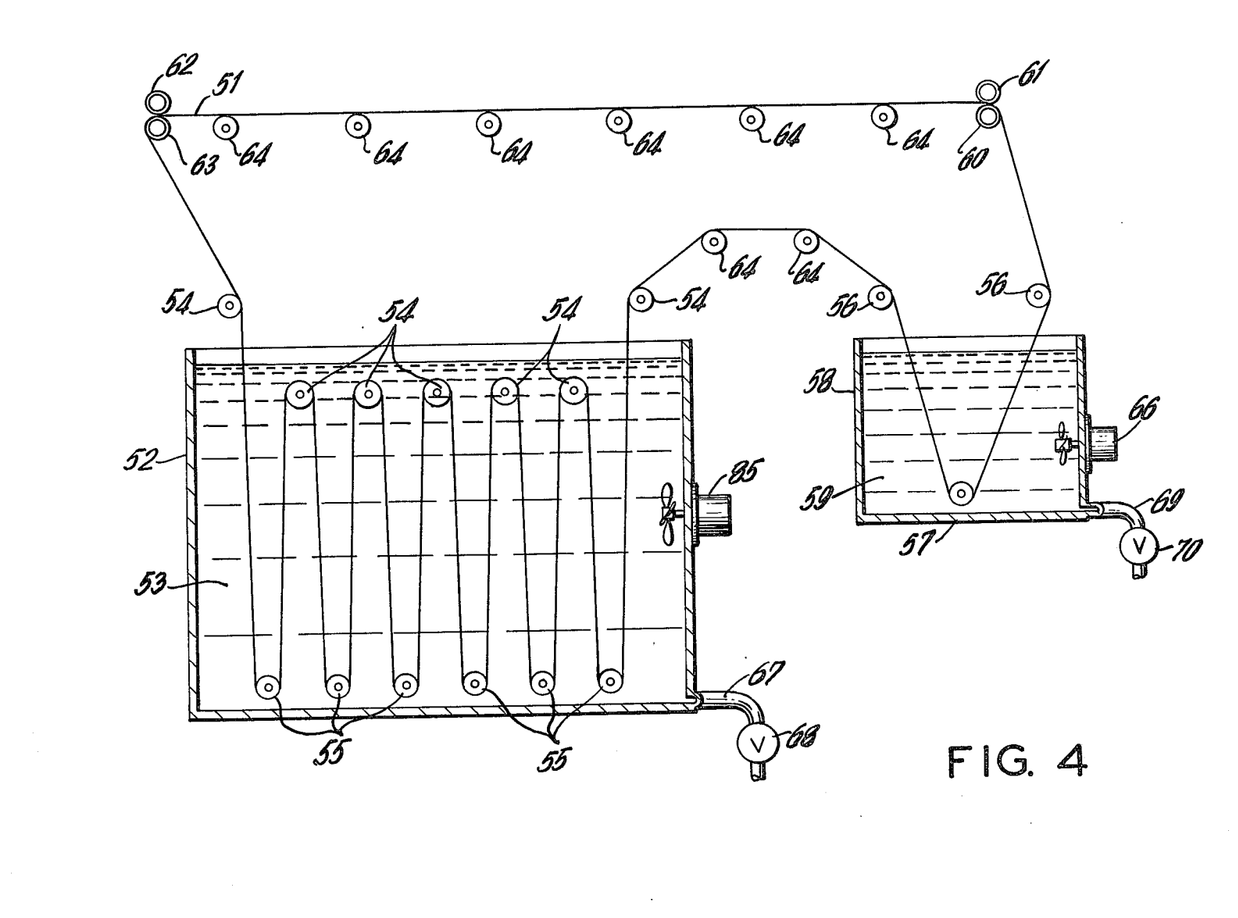
FIG. 4 is a mechanical schematic diagram of apparatus in accordance with an additional embodiment of this invention for concentrating and purifying antigens and antibodies.

FIG. 4 is a mechanical schematic diagram of an apparatus in accordance with this invention for concentrating and purifying antigens and antibodies. It will aid in understanding the embodiment of FIG. 4 to realize at the outset that in operation, the FIG. 4 embodiment is a modification of the FIG. 3 embodiment just discussed. In FIG. 4, a continuous flexible belt of substrate material 51 which is coated with a monomolecular layer of antigen which specifically reacts with the antibody to be concentrated and purified is first introduced into a container 52 which contains a quantity of liquid 53 which includes the antibody to be purified. Immunological complexing between antigen and antibody takes place in container 52 and then substrate 51, now containing a bimolecular antigen-antibody layer, proceeds to container 58 containing the immunological bond-cleaving reagent solution 59 which severs the immunological bond between the two biological constituents thereby collecting the molecules of the second layer in solution 59. Upon exiting container 58 therefore substrate 51 again has thereon only the original monomolecular layer. Substrate 51 is then returned to container 52 to again pick up a monomolecular layer of the antibody to be collected which is again stripped off in container 58. Belt 51 is driven through aqueous media 53 and 59 by capstans 60 and 63 operating cooperatively with respectively pinch rollers 61 and 62. Capstans 60 and 63 may be driven by any suitable means which may conveniently be small electric motors coupled to capstans 60 and 63 by speed reducing gear trains. Because the immunological complexing reaction is a much slower reaction than the bond-severing reaction, it is desirable for efficiency that coated substrate belt 51 be in contact with aqueous medium 53 containing the antibody to be collected for a much greater time than it is in contact with the cleaving reagent solution 59. Accordingly, it is desirable that container 52 be substantially larger than container 58 and that a plurality of upper and lower idler rollers 54 and 55, respectively, be provided for causing multiple passage of belt 51 through aqueous medium 53. This provides for a greater length of belt 51 being in contact with aqueous medium 53 at any given time and therefore for any given segment of belt 51 being exposed to aqueous medium 53 for a greater period of time. On the other hand, a single passage of belt 51 through the cleaving reagent solution 59 is quite sufficient to strip the second layer therefrom. Accordingly, a pair of upper idler rollers 56 and a single idler roller 57 are provided for guiding belt 51 through solution 59. A plurality of idler rollers 64 are provided as required to mechanically support belt 51 during its passage between containers 52 and 58. Containers 52 and 58 are preferably provided with agitating means 65 and 66, respectively, which fluid-sealingly penetrate the walls thereof for agitating solutions 53 and 59 to ensure the refreshment of the solutions in contact with belt 51. Container 52 is provided with drain pipe 67 controlled by valve 68 for draining solution 53 therefrom when the concentration of the desired antibody therein has been decreased to the point at which efficient collection thereof is no longer possible. A fresh sample of aqueous medium 53 may then be added to container 52 through the open upper end thereof. Container 58 is provided with drain pipe 69 controlled by valve 70 for draining off the desired solution of purified antibody of the cleaving reagent when the desired concentration has been reached. A fresh charge of the cleaving reagent may similarly be added to container 58 through the open upper end thereof. Since as disclosed above with reference to FIG. 3, substrate belt 51 may be coated with any desired antigen or antibody, the method and apparatus of FIG. 4 is useful for collecting a purified concentration of any arbitrary antigen or antibody desired so long as an immunological reaction involving the desired antigen-antibody pair exists. Additionally, by slightly modifying its operation, the apparatus of FIG. 4 may be used to selectively remove a specific undesired antigen or antibody from a mixture such as a serum. To accomplish this, the apparatus of FIG. 4 is simply run for an extended period of time without refreshment of aqueous medium 53 and with periodic refreshement as may be required of solution 59. In this case, the product obtained at drain pipe 67 is serum 53 from which the undesired antigen or antibody has been eliminated to any required degree depending only on the time of operation of the system.

The above-described operation may be modified so that the cleaving reagent solution 59 is applied on the surface of a second substrate, e.g. a belt. The first substance, e.g. belt containing the bimolecular layer touches or abuts the second substrate thereby leaving the specifically reacting antibody adhered to the second substrate as a monomolecular layer. The second substrate can be of the same type and composition as described above for the first substrate.

It should be noted that the configuration of the substrate used herein is not critical to the invention. It can be slide shaped, e.g., in the form of metallized glass slides because of the ready availability of such slides. However, if the belt operation is to be followed, it will be in the form of a belt. For instance, the substrate can comprise a plurality of metallized slides affixed to a flexible belt. The only limitation imposed on a substrate is its ability to allow the formation of a monomolecular layer thereon. The dimensions or form will be dictated by the manner in which the procedure is carried out including subsequent analysis and its objective. If it is for collection of a particular immunologically active biological constituent a belt is preferred.

DESCRIPTION OF THE PREFERRED EMBODIMENTS

The following examples, which are to be regarded as illustrative and not limiting, show how antigens and antibodies are purified and are collected according to this invention.

EXAMPLE 1

A procedure for isolating hepatitis antibody is carried out as follows: A glass slide is metallized with a layer of indium metal globules and immersed in a solution of 1 mg./ml. of hepatitis-associated antigen in 0.85% saline. The slide is removed and incubated in a moist chamber (plastic box filled with wet sponges) at 23° C. until the antigen adheres to the metallized surface (10–30 minutes). The slide is washed with distilled water and blown dry with a jet of air. The slide can be stored for later use or used immediately. The slide is then exposed to a preparation made from rabbit or goat blood serum which contains antibody to hepatitis-associated antigen. The slide and antibody solution are incubated at 37° C. in a plastic box attached to a shaker, for approximately 15 minutes. After incubation, the slide is again washed with distilled water. The slide is then immersed in a solution of citric acid (0.1N) with agitation. The resulting slide contains monomolecular layer of antigen and is available for reuse and the citric acid solution contains pure antibody, whose isolation is effected using standard techniques.

EXAMPLE 2

A procedure for isolating gonorrhoea antibodies is carried out as follows: A glass slide is metallized with a layer of titanium and the surface layer is then oxidized to produce a cover layer of an oxide of titanium. The slide is immersed in a Neisseria gonorrhoeae extract dissolved in salt water to produce a concentration of 1 mg./ml. The slide is incubated in a moist chamber (plastic box filled with wet sponges) at room temperature (23° C.) until the antigen adheres to the oxide surface (10–30 minutes). The slide is washed with distilled water and blown dry with a jet of air. The slide can be stored at this point for later use. The slide is then immersed in a preparation made from rabbit or goat blood serum which contains antibody to the Neisseria antigen. Total volume is 2 ml. The slide and antibody solution are incubated at 37° C. in a plastic box attached to a shaker, for approximately 15 minutes. After incubation, the slide is again washed with distilled water. The slide is then immersed in a solution of citric acid (0.1 N) with agitation. The resulting slide contains monomolecular layer of antigen and is available for reuse and the citric acid solution contains pure antibody, whose isolation is effected using standard techniques.

EXAMPLES 3-10

Purification procedures according to this invention are carried out by the procedure of Example 1 substituting the following substrates, antigens, compounds and antibody preparations:

| Example | Substrate | Antigen | Antibody Source |
|---|---|---|---|
| 3 | indium metallized glass | hepatitis-associated | rabbit blood serum |
| 4 | indium metallized glass | hepatitis-associated | rabbit blood serum |
| 5 | gold metallized glass | hepatitis-associated | rabbit blood serum |
| 6 | tantalum metallized glass | hepatitis-associated | rabbit blood serum |
| 7 | gold metallized glass | rubella virus extract | rabbit blood serum |
| 8 | gold metallized glass | polio virus extract | rabbit blood serum |
| 9 | gold metallized glass | vesicular stomatitis virus extract | rabbit blood serum |
| 10 | gold metallized glass | Treponema pallidum suspension (syphilis) | rabbit blood serum |

In addition to the above specific examples, an isolation procedure may be carried out in accordance with this invention using slide shaped substrates metallized with gold or tantalum upon which are deposited aqueous solutions of the following antigenic preparations:

tetanus toxoid (tetanus)
diphtheria toxin (diphtheria)
asperigillus extract (fungus)
candida extract (fungus)
toxoplasma gondii (parasite)
nucleoprotein and DNA
thyroglobulin (Hashimoto's disease)
collagen fractions
human chorionic gonadotrophin (pregnancy)
insulin
keyhole lymphet hemocyanin (antibody response)
pencillinase extract (large enzyme)

EXAMPLE 11

The procedures of Examples 1-10 can be carried out in a cyclic fashion wherein a substrate in belt form coated with a monomolecular layer of antigen is introduced into a container which contains a second aqueous medium containing the antibody to be purified. The so-treated belt containing a bimolecular layer is then immersed into a container containing weak acid (0.1N citric acid), preferably while agitating, severing the immunological bond leaving the second or outer layer component in the citric acid solution for eventual recovery and the substrate having a monomolecular layer of first antigen which is recycled to the first aqueous medium and then to the acid solution.

While this invention has been described with reference to particular embodiments and examples, other modifications and variations will occur to those skilled in the art, in view of the above teachings. Accordingly, it should be understood that within the scope of the appended claims, the invention may be practiced otherwise than is specifically described.

I claim:

1. A method of preparing a purified concentration of an immunologically reactive antibody comprising the steps of immersing a belt of substrate material in an aqueous medium containing a corresponding specifically reacting antigen to said antibody to coat said belt with a monomolecular layer of said antigen; immersing a portion of said belt in an aqueous medium containing said antibody to complex said antigen with said antibody; immersing said portion of said belt in a weak acid solution to cleave bonds between said antigen and said antibody, thus forming a solution of said antibody in said weak acid solution and leaving said antigen coated on said belt; and recovering said antibody from said solution.

2. A method as defined in claim 1 of preparing a purified concentration of an immunologically reactive purified antigen wherein a specifically reacting antibody is substituted for the antigen and the corresponding immunologically reactive antigen is substituted for the antibody.

3. A method as defined in claim 1 wherein said antigen is a protein antigen, said antibody is a protein antibody specific to the antigen and said aqueous media are solutions.

4. A method as defined in claim 2 wherein said antibody is a protein antibody, said antigen is a protein antigen specific to the antibody and said aqueous media are solutions.

5. A method of purifying an immunologically reactive antibody comprising the steps of immersing a substrate in an aqueous medium containing a corresponding specifically reacting antigen to said antibody to coat said substrate with a monomolecular layer of said antigen; immersing said substrate in an aqueous medium containing said antibody to complex said antigen with said antibody; immersing said substrate in a weak acid solution to cleave bonds between said antigen and said antibody, thus forming a solution of said antibody in said weak acid solution and leaving said antigen coated on said substrate; and recoverying said antibody from said solution.

6. A method as defined in claim 5 of purifying an immunologically reactive antigen wherein a specifically reacting antibody is substituted for the antigen and the corresponding immunologically reactive antigen is substituted for the antibody.

7. A method as defined in claim 5 wherein said antigen is a protein antigen, said antibody is a protein antibody specific to the antigen and said aqueous media are solutions.

8. A method as defined in claim 6 wherein said antibody is a protein antibody, said antigen is a protein antigen specific to the antibody and said aqueous media are solutions.

9. A method of purifying an immunologically reactive antibody comprising the steps of immersing a first substrate in an aqueous medium containing a corresponding specifically reacting antigen to said antibody, immersing said first substrate in an aqueous medium containing said antibody to complex said antigen with said antibody, applying a weak acid solution to a surface of a second substrate to cleave bonds between said antigen and said antibody, abutting a surface of said first substrate having said antigen and antibody thereon to said surface of said second substrate having said weak acid solution thereon, separating said substrates whereby said antibody adheres to said surface of said second substrate in monomolecular layer, and recovering said antibody.

10. A method as defined in claim 9 wherein a specifically reacting antibody is substituted for the antigen and the corresponding immunologically reactive antigen is substituted for the antibody.

11. A method as defined in claim 9 wherein said antigen is a protein antigen, said antibody is a protein antibody specific to the antigen and said aqueous media are solutions.

12. A method as defined in claim 10 wherein said antigen is a protein antigen, said antibody is a protein antibody specific to the antigen and said aqueous media are solutions.

13. A method as defined in claim 1 further including the steps or agitating said aqueous medium containing said immunologically reactive antibody, and agitating said weak acid solution.

14. A method as defined in claim 13, wherein said antigen is a protein antigen, said antibody is a protein antibody specific to the antigen and said aqueous media are solutions.

15. A method as defined in claim 13 wherein said agitating of said aqueous medium and said weak acid solution is performed continuously.

16. A method as defined in claim 13 further including the step of periodically draining and refreshing said aqueous medium containing said immunologically reactive antibody.

17. A method as defined in claim 16 wherein said purified immunologically reactive antibody is collected by draining said weak acid solution and further including the step of refreshing said weak acid solution after said draining.

18. A method as defined in claim 9 comprising the additional step of applying a metal coating to said surface of a second substrate prior to applying said weak acid solution thereto to cleave bonds between the antigen and the antibody.

19. A method as defined in claim 5 wherein said substrate is a metallized slide.

20. A method as defined in claim 19 wherein the metal comprising the substrate is selected from indium, gold, silver, tin and lead.

21. A method as defined in claim 20 wherein the substrate comprises indium on a glass slide.

22. A method as defined in claim 20 wherein the substrate comprises gold on a glass slide.

23. A method as defined in claim 20 wherein the substrate comprises a glass slide coated with a thin indium layer and overcoated with a gold layer.

24. A method as defined in claim 20 wherein the metallized slide also includes a metal oxide layer intermediate the metal of the slide and said monomolecular layer.

25. A method as defined in claim 24 wherein said metal is titanium and said oxide is an oxide of titanium.

26. A method as defined in claim 19 wherein said antigen is a protein antigen, said antibody is a protein antibody specific to the antigen and said aqueous media are solutions.

27. A method as defined in claim 1 wherein said substrate comprises a plurality of metallized slides affixed to a flexible belt.

28. A method as defined in claim 27 wherein the metal comprising the substrate is selected from indium, gold, silver, tin and lead.

29. A method as defined in claim 28 wherein the substrate comprises indium on a glass slide.

30. A method as defined in claim 28 wherein the substrate comprises gold on a glass slide.

31. A method as defined in claim 28 wherein the substrate comprises a glass slide coated with a thin indium layer and overcoated with a gold layer.

32. A method as defined in claim 28 wherein the metallized slide also includes a metal oxide layer intermediate the metal of the slide and said monomolecular layer.

33. A method as defined in claim 32 wherein said metal is titanium and said oxide is an oxide of titanium.

34. A method as defined in claim 27 wherein said antigen is a protein antigen, said antibody is a protein antibody specific to the antigen and said aqueous media are solutions.

35. A method of preparing a purified concentration of an immunologically reactive antibody comprising the steps of immersing a belt of substrate material in an aqueous medium containing a corresponding specifically reacting antigen to said antibody to coat said belt with a monomolecular layer of said antigen; immersing a portion of said belt in an aqueous medium containing said antibody to complex said antigen with said antibody; immersing said portion of said belt in a solution of an immunological bond-cleaving reagent to cleave bonds between said antigen and said antibody, said solution being selected from the group of a base solution and a strong salt solution, thus forming a solution of said antibody in said bond-cleaving reagent solution and leaving said antigen coated on said belt; and recovering said antibody from said solution.

36. A method of purifying an immunologically reactive antibody comprising the steps of immersing a substrate in an aqueous medium containing a corresponding specifically reacting anitgen to said antibody to coat said substrate with a mono-molecular layer of said antigen; immersing said substrate in an aqueous medium containing said antibody to complex said antigen with said antibody; immersing said substrate in a solution of an immunological bond-cleaving reagent to cleave bonds between said antigen and said antibody said solution being selected from the group of a base solution and a strong salt solution, thus forming a solution of said antibody in said bond-cleaving reagent solution and leaving said antigen coated on said substrate; and recovering said antibody from said solution.

37. A method of purifying an immunologically reactive antibody comprising the steps of immersing a first substrate in an aqueous medium containing a corresponding specifically reacting antigen to said antibody, immersing said first substrate in an aqueous medium containing said antibody to complex said antigen with said antibody, applying a bond-cleaving reagent solution selected from the group of a base solution and a strong salt solution to a surface of a second substrate, to cleave bonds between said antibody and said antigen, abutting a surface of said first substrate having said antigen and antibody thereon to said first substrate having said antigen and antibody thereon to said surface of said second substrate having said bond-cleaving reagent solution thereon, separating said substrate whereby said antibody adheres to said surface of said second substrate in a monomolecular layer, and recovering said antibody.

* * * * *